United States Patent [19]
Fenton, Jr.

[11] Patent Number: 6,056,751
[45] Date of Patent: May 2, 2000

[54] SUTURELESS SOFT TISSUE FIXATION ASSEMBLY

[75] Inventor: Paul V. Fenton, Jr., Marblehead, Mass.

[73] Assignee: Axya Medical, Inc., Beverly, Mass.

[21] Appl. No.: 09/061,473

[22] Filed: Apr. 16, 1998

[51] Int. Cl.[7] .................................................. A61B 17/03
[52] U.S. Cl. ................................ 606/72; 606/73; 606/75; 606/151; 606/232
[58] Field of Search ............................ 606/72, 73, 75, 606/151, 213, 232; 156/73.1

[56] References Cited

U.S. PATENT DOCUMENTS

| | | | |
|---|---|---|---|
| 4,434,796 | 3/1984 | Karapetian et al. | 606/75 |
| 4,870,957 | 10/1989 | Goble et al. | 606/73 |
| 5,013,316 | 5/1991 | Goble et al. | 606/72 |
| 5,413,585 | 5/1995 | Pagedas | 606/151 |
| 5,725,541 | 3/1998 | Anspach, III et al. | 606/151 |

*Primary Examiner*—Michael Buiz
*Assistant Examiner*—David O. Reip
*Attorney, Agent, or Firm*—McDermott, Will & Emery

[57] ABSTRACT

A soft tissue fixation assembly comprises an anchor element which is installed in a bone or other tissue, and a joiner element which mates with the anchor element to define a tissue capture region between them. A section of soft tissue is held within the tissue capture region, and energy is transmitted into the joiner element to cause relative vibratory motion between the respective components and localized melting of the contacting portions of the respective components to establish a welded joint. The soft tissue segment is thus fixed to the bone without sutures or other fasteners.

23 Claims, 4 Drawing Sheets

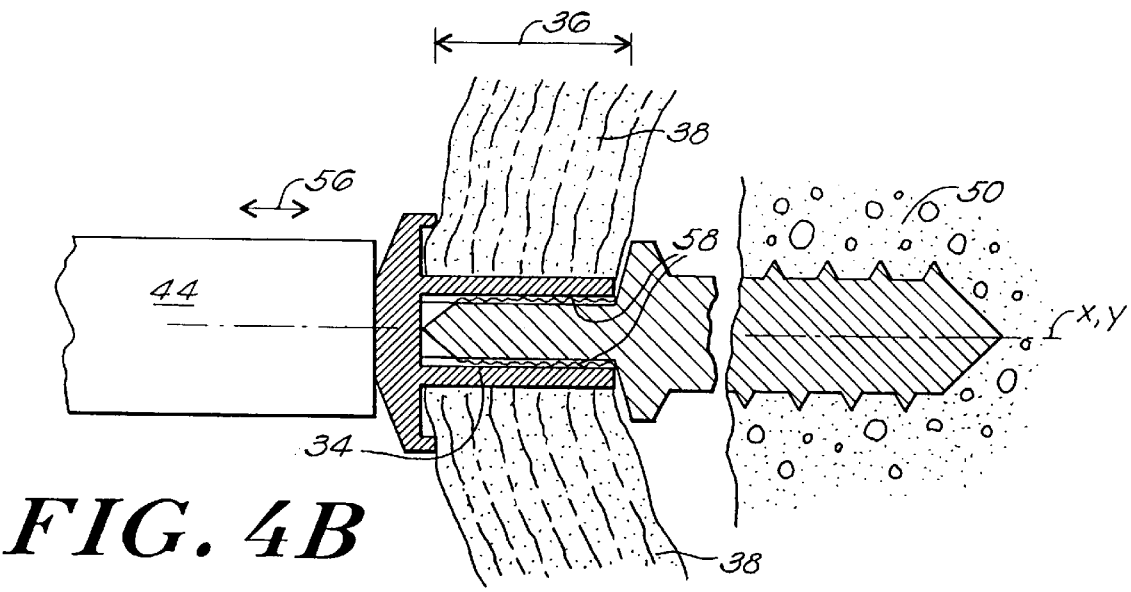
FIG. 4B
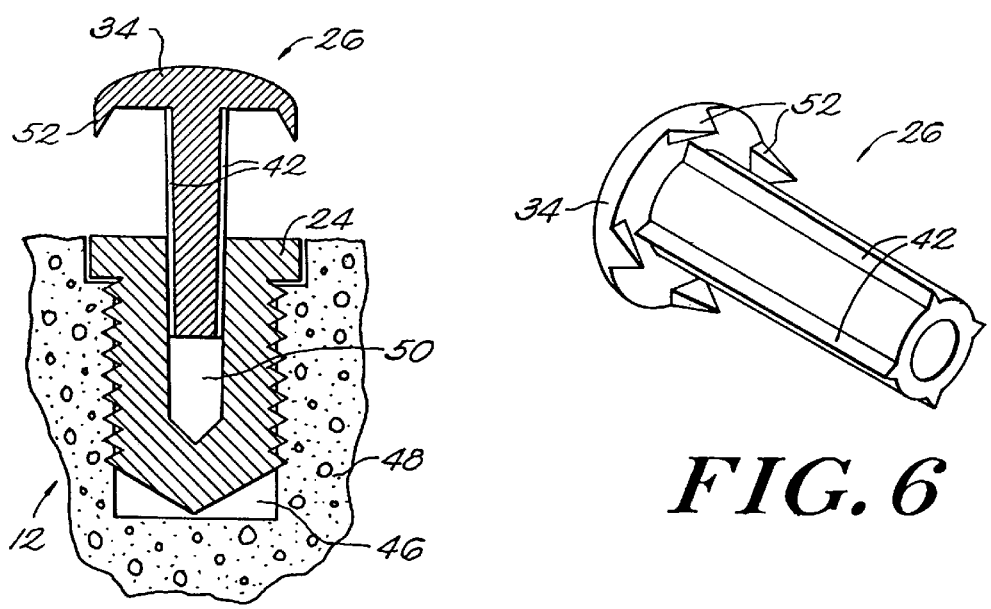
FIG. 5
FIG. 6

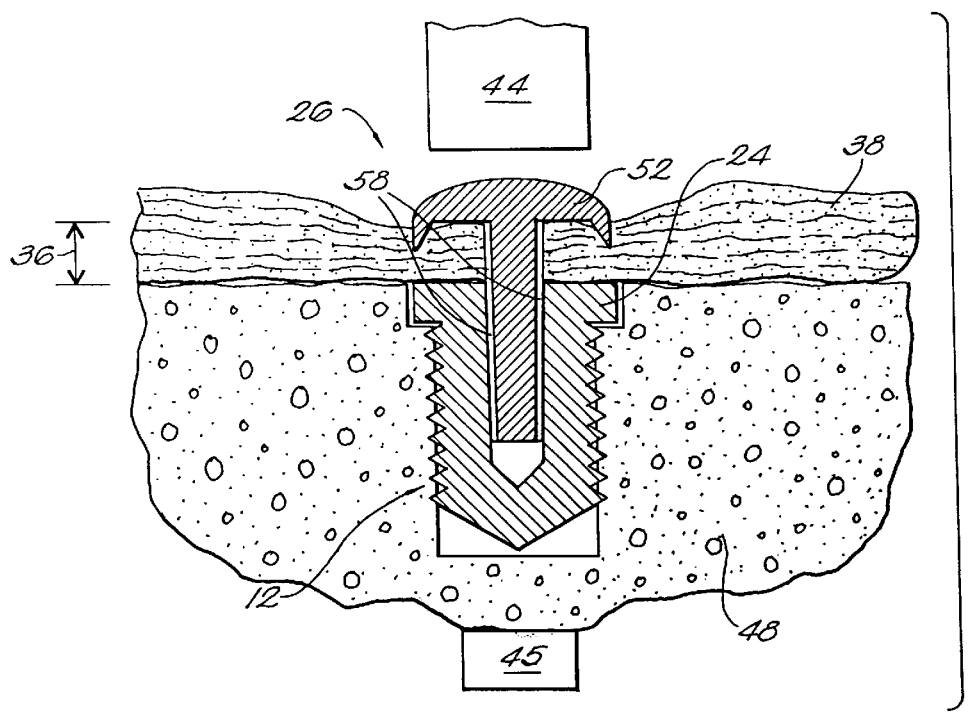
FIG. 7
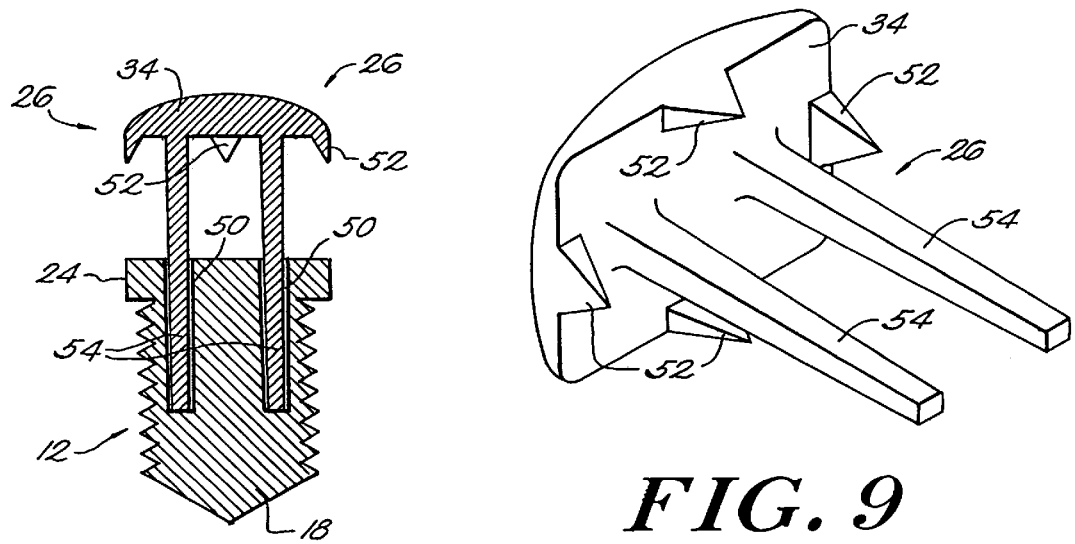
FIG. 8
FIG. 9

SUTURELESS SOFT TISSUE FIXATION ASSEMBLY

FIELD OF THE INVENTION

The invention is related to surgical fixation devices for fixing soft tissue to bone, and in particular to soft tissue fixation devices which do not require sutures.

BACKGROUND OF THE INVENTION

In the surgical repair of soft tissue, such as, for example, the surgical reattachment of a torn ligament to bone, it is known to use multi-part devices to fix the soft tissue to the bone. The multi-part devices typically include a screw or other bone anchoring device, and a button-like device for anchoring the suture therein. The anchor is installed in a predrilled hole in the bone, and the soft tissue is fixed to the anchor in the bone with sutures, which are fastened together with the button instead of with knots.

A disadvantage of such devices is that the quality and strength of the device may be limited by the quality and strength of the suture, and/or by the integrity of the attachment of the device to the bone. The soft tissue will detach from the anchor in the bone if the suture slips or breaks. If the anchor or the button slips or becomes dislodged, the soft tissue will not remain anchored to the bone.

Another disadvantage of such a device is its multi-part nature. It is difficult to join the button and the anchor with a suture and maintain the button appropriately oriented with respect to the anchor and to the tissue while the suture is appropriately tensioned and fastened in situ.

It would therefore be an advantage to provide a surgical soft tissue fixation device which overcomes the disadvantages of the prior art devices.

SUMMARY OF THE INVENTION

The invention provides an integrated soft tissue fixation assembly which attaches soft tissue segments to bone without the need for sutures. The assembly includes two pieces which are fused together in situ in a patient and which compress soft tissue segments in a defined volume within the assembly.

According to one aspect of the invention, there is provided a sutureless soft tissue fixation assembly for attachment of soft tissue to bone. The assembly comprises:
 a bone anchor element adapted for installation into a hole in a bone and including an anchor portion at a leading end and a drive portion at a trailing end; and
 a joiner element.
The anchor element and the joiner element are adapted to be joined together in situ. As assembled, they define a tissue capture region between them.

The joiner element is, in one embodiment, in the form of a post with a cap at one end. The anchor element preferably includes threads or barbs at its leading end for substantially permanent installation of the anchor portion into a bone. The anchor element is adapted for mating engagement with the joiner element and includes a radially extending hub and, in one embodiment, at least one bore for receiving a corresponding pin or leg of the joiner element. One or both of the anchor element and the joiner element includes one or more energy directors for focusing energy applied to either component of the assembly.

The energy directors preferably focus ultrasonic energy applied to the assembly and comprise a plurality of protruding elements that extend outwardly from one or both components.

According to another embodiment, the joiner element includes a bore for receiving a complementary pin or leg of the anchor element. At least one of the bore of the joiner element and the anchor element includes one or more energy directors for focusing energy applied to the assembly.

The cap portion of the post-type joiner element includes one or more protruding elements adapted to extend into and hold the soft tissue in place within the tissue capture region of the assembly. The protruding elements may comprise barbs extending from the periphery of the cap portion into the tissue capture region.

The tissue capture region of the assembly is defined as the annular region between the cap portion of the post-type joiner element and the hub of the anchor element. In one embodiment, the hub of the anchor element is located at a trailing end of the anchor element opposite the leading end. In another embodiment, the hub of the anchor element is located between the leading and trailing ends of the anchor element.

According to another aspect of the invention there is provided a method of fixing soft tissue to a bone without using sutures. The method comprises the steps of:
 providing a soft tissue fixation assembly as described above for sutureless attachment of soft tissue to bone;
 drilling a hole into a bone at a desired location for installation of the anchor element therein;
 installing the anchor element into the drilled hole;
 placing a segment of soft tissue to be anchored to the bone over the anchor element in the bone;
 assembling the joiner element into the anchor element through the segment of soft tissue to hold the soft tissue segment within the tissue capture region; and
 bonding the joiner element to the anchor element, thereby fixing the soft tissue segment to the bone.

The step of bonding the joiner element to the anchor element preferably comprises the step of transmitting ultrasonic energy to the joiner element to effect vibratory motion of the joiner element relative to the anchor element and localized melting and bonding of interfering portions of the two components.

According to another embodiment of the invention, there is provided a soft tissue fixation assembly for sutureless attachment of soft tissue to bone. The assembly comprises:
 one or more bone anchor elements adapted for installation into respective holes in a bone, each bone anchor element including an anchor portion at a leading end and a drive portion at a drive end; and
 a band element adapted for bonded engagement with each anchor element to define a tissue capture region between the band and the bone anchor elements.

In one preferred embodiment, the assembly includes a pair of bone anchor elements, and the band element extends between opposed ends which are adapted for bonded engagement with corresponding structures on the bone anchor elements.

In another preferred embodiment, the assembly includes a single bone anchor element, and the band element comprises a loop. The ends of the loop are adapted for bonded engagement with the bone anchor element, and the tissue capture region is defined as the region within the loop.

These and other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 4B is a side elevational view of the components of the assembly shown in FIG. 1 after assembly;

FIG. 5 is a sectional view of a soft tissue fixation assembly according to another embodiment of the invention;

FIG. 6 is a perspective view of the post-type joiner element of the assembly shown in FIG. 5;

FIG. 7 is a diagram illustrating the assembly shown in FIG. 5 in use;

FIG. 8 is a sectional view of an alternate embodiment of the assembly of FIG. 5;

FIG. 9 is a perspective view of the post-type joiner element of the assembly of FIG. 8;

Like elements in the respective FIGURES have the same reference numbers.

DETAILED DESCRIPTION OF THE PREFERRED EMBODIMENT

Figure 1:
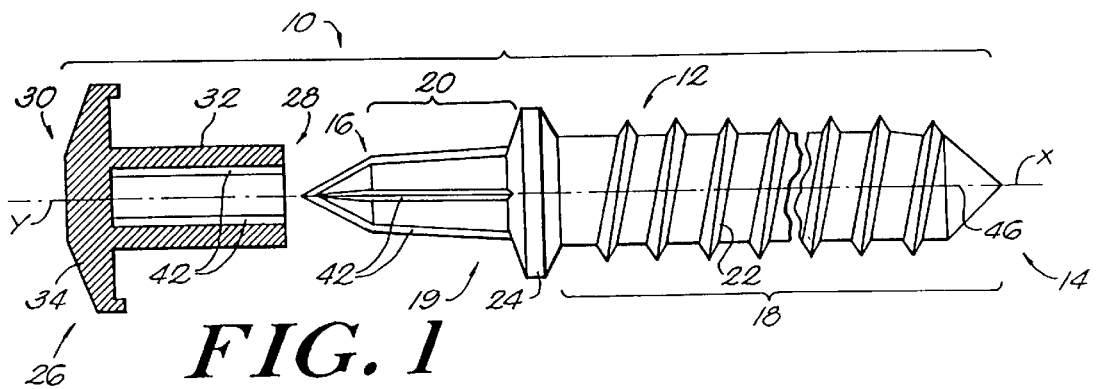
FIG. 1 is a side elevational view of a soft tissue fixation assembly according to one aspect of the invention.

One embodiment of the soft tissue fixation assembly of the present invention is illustrated in FIG. 1. The assembly 10 comprises an elongated anchor element 12 which extends along an axis X between leading end 14 and trailing end 16. The anchor element 12 includes an anchor portion 18 at its leading end 14 and a drive portion 19 at its trailing end 16. In this embodiment a leg or pin 20 extends away from the anchor portion 18 and forms the male portion of a male/female connection within the assembly, detailed more fully below. The anchor portion 18 is adapted, such as by threads or barbs 22 on the outer surface thereof, to grip a bone into which the anchor element is to be installed. In this embodiment, the anchor portion 18 and pin 20 of the anchor element are separated by a hub 24 located between the leading and trailing ends of the anchor element and extending radially outward from the anchor element. The hub 24 has a diameter which is greater than the nominal diameters of either the anchor portion or the pin 20 so that, in one embodiment, the hub 24 acts as a stop for the anchor element 12 during installation into a bone.

The assembly illustrated in FIG. 1 further comprises a joiner element 26 which extends along an axis Y between opposed ends 28, 30. In one preferred embodiment, the joiner element 26 is preferably in the form of a post which includes a receptacle portion 32 at one end 28 and a cap 34 at the other end 30.

Figure 4A:
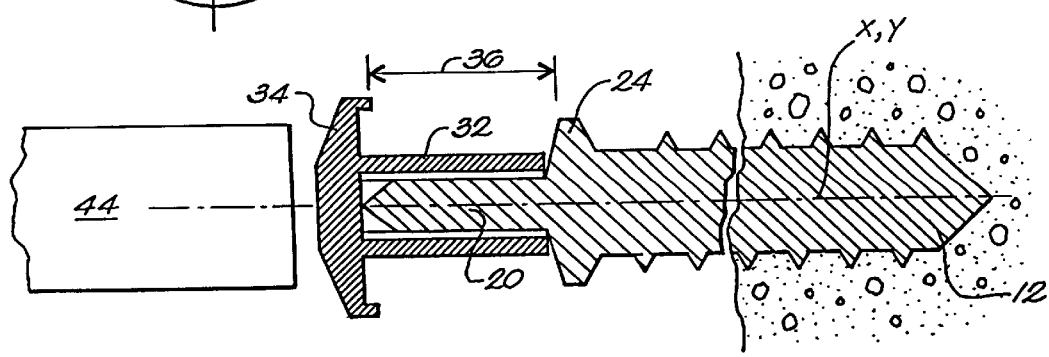
FIG. 4A is a side elevational view of the components of the assembly shown in FIG. 1 prior to assembly.

The anchor element 12 and joiner element 26 are each adapted for substantially permanent attachment to each other in situ in a patient, preferably by ultrasonic welding of at least a portion of the pin 20 of the anchor element 12 and the receptacle portion 32 of the post-type joiner element, as detailed more fully below. The components thus assembled extend along common axes X, Y and define a tissue capture region 36, shown best in FIGS. 4A and 4B, between the hub 24 on the anchor element 12 and the cap portion 34 on the joiner element 26. Soft tissue segment 38, shown in phantom in FIG. 4B, are captured and gently compressed within the tissue capture region 36 and held by a combination of compressive and frictional forces within the assembly 10 in a fixed relationship to the bone, without the need for sutures or other fastening devices.

Figure 2:
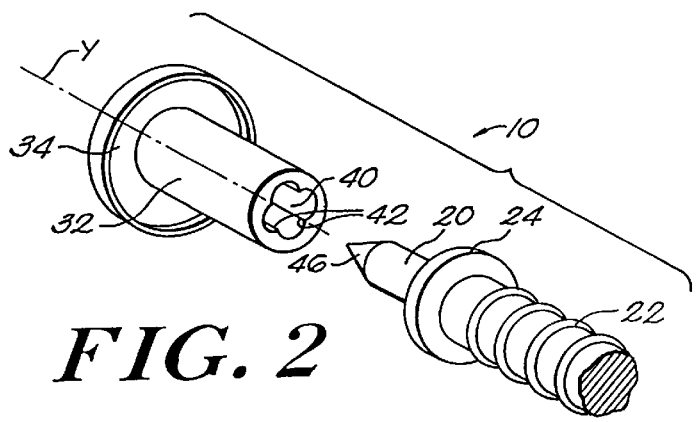
FIG. 2 is a perspective view of the soft tissue fixation assembly of FIG. 1.

A perspective view of the assembly of FIG. 1 is shown in FIG. 2. The receptacle portion 32 of the post-type joiner element includes a bore 40 which is sized to accommodate the pin 20 of the anchor element. In one embodiment, the bore 40 includes one or more energy directors 42, in the form of, for example, ribs, projections or spines which extend radially from the bore surface, as shown most clearly in FIG. 3. The energy directors 42 focus ultrasonic energy directed into the joiner element from an ultrasonic weld horn 44, as shown in FIGS. 4A and 4B, and establish an interference between the bore of the joiner element and the pin of the anchor element.

In another preferred embodiment, energy directors 42 in the form of ribs, projections, spines or the like can alternatively, or additionally, be located on the outer surface of the pin 20 of the anchor element 12, as shown in FIG. 1.

A second embodiment of the invention is illustrated in FIGS. 5, 6 and 7, and a third embodiment is illustrated in FIGS. 8 and 9. According to the second embodiment, the anchor element 12 includes a hub 24 which is at or near the trailing end of the anchor element and forms a flange which sits within a counterbored or countersunk hole 46 in a bone 48. The anchor element of this embodiment forms the female portion of a male/female connection and includes at least one bore 50 adapted to receive the joiner element 26.

The joiner element 26 includes one or more energy directors 42 extending radially from the joiner element 26, as shown in FIG. 6. The cap portion 34 of the post-type joiner element can include one or more barbs or similar structures 52 which extend from the cap toward the tissue capture region 36 of the assembly and are adapted to pierce or penetrate soft tissue held in the tissue capture region of the assembly in order to facilitate fixation of the soft tissue to the bone.

Another embodiment of the invention is shown in FIGS. 8 and 9. As shown best in FIG. 8, the anchor element 12 includes a plurality of bores 50 adapted to receive the prongs or legs 54 of a multi-pronged joiner element 26, shown in greater detail in FIG. 9.

The assembly of FIG. 1 in use is illustrated in FIGS. 4A and 4B, and the assembly of FIG. 5 in use is illustrated in FIG. 7. The two components of the assembly are joined by ultrasonic welding in situ in a patient. The anchor portion 18 of the anchor element 12 is inserted and threaded into a predrilled hole in a bone. If desired, the anchor portion 18 can include a self-drilling tip so that the anchor element 12 can be driven directly into a bone without predrilling a hole first. The pin 20 of the anchor element 12 is inserted into the receptacle portion 32 of the joiner element 26, as shown in FIG. 4A. The weld horn 44 is placed in contact with the joiner element 26, and ultrasonic energy is transmitted from one or more transducers (not shown) associated with the weld horn 44 into the joiner element 26. The anchor element 12 is fixed in the bone, which may act as a stationary anvil for the weld horn 44, and thus the anchor element is held stationary as well. Alternatively, an L-shaped or other suitably shaped horn and anvil structure can be used to provide ultrasonic energy into a relatively confined space. Transmission of ultrasonic energy into the post element 26 from the weld horn 44 causes vibration of the joiner element 26 relative to the anchor element 12 in the direction of arrows 56, shown in FIG. 4B. Friction caused by the relative movement of the joiner element 26 against the anchor element 12, and in particular the relative movement of the energy directors 42 against the interfering portions of the stationary component, causes localized melting of the energy directors 42 and the corresponding interfering portions of the stationary component to create weld regions 58.

Figure 3:
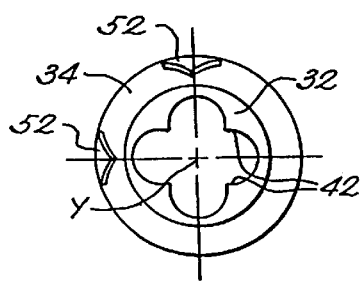
FIG. 3 is an axial view of a post-type joiner element of the assembly shown in FIG. 1.

The energy directors 42 can have any configuration which provides a strong and permanent attachment of the anchor element 12 to the joiner element 26. For example, instead of axial ribs or spines, as illustrated in FIGS. 2 and 3, the energy directors 42 can be in the form of helical ribs or threads on the surface of the bore or of the pin on the respective components.

The region between the hub 24 on the anchor element 12 and the cap portion 34 of the joiner element 26 defines the tissue capture region 36, shown in FIGS. 4A and 4B. Soft tissue such as, for example, a ligament 38, is held and gently yet firmly compressed between the radially extending hub 24 and the end cap 34 and is thus held in place relative to the bone into which the anchor element 12 is installed. No sutures are required to hold the soft tissue in place, and the assembly 10 is fused into a single piece in situ so that all parts of the assembly are integral and do not move relative to one another. The tissue segments 38 are held in atraumatic compression in the tissue capture region 36 of the assembly and thus do not move relative to either the assembly or the bone in which the assembly is installed.

A method of fixing soft tissue to bone employing a soft tissue fixation assembly as disclosed herein is also considered to be within the scope of the invention. According to the method, a soft tissue assembly as disclosed herein is provided for the fixation of one or more segments of soft tissue to a bone or other tissue. The anchor portion of the anchor element 12 is installed into a bone at a predetermined location, either in a predrilled hole or by self-tapping a hole at the desired location. The joiner element 26 is mated with the anchor element 12 as installed in the bone. An ultrasonic weld horn 44 is placed in contact with the joiner element 26, and ultrasonic energy is transmitted into the joiner element 26 to cause vibration of the joiner element relative to the anchor element 12, which is in contact with a stationary anvil 45 and thus remains substantially stationary. The relative movement of the joiner element and the anchor element causes localized melting of the energy directors 42 and the corresponding interfering portions of the respective components, thereby fusing or welding the two components of the assembly at weld regions 58 and capturing the soft tissue 38 within the tissue capture region 36.

The assembly 10 is preferably made of a thermoplastic material which can be joined by ultrasonic welding. If desired, the anchor portion 18 of the anchor element 12 can be made of a harder material, such as, for example, titanium, so that the assembly includes an anchor portion having a self-drilling and self-tapping tip for drilling and tapping a hole into the bone. In addition, the joiner element 26 may also be made of a harder material, such as titanium, to provide a more efficient transmission of ultrasonic and/or vibratory energy to the cap element. Any materials can be used, provided that the portions of the assembly which fuse together to bond the parts are made of a material suitable for transmission of ultrasonic energy and capable of being melted and joined together in a welded joint.

The tissue capture region 36 can be designed to be of any appropriate dimension for the tissue to be attached. In one embodiment, illustrated in FIGS. 1, 2, 3, 4A and 4B, the size of the tissue capture region 36 is determined by the location of the hub 24 on the anchor element. In another embodiment, illustrated in FIGS. 5-9, the size of the tissue capture region is determined by the extent of engagement, or depth of penetration, of the components with each other. For example, in the embodiment of FIG. 5, if the length of the bore 50 is less than the length of the joiner element, a portion of the joiner element will extend above the hole in the bone to define an annular tissue capture region extending radially about that portion of the joiner element.

Figure 10:
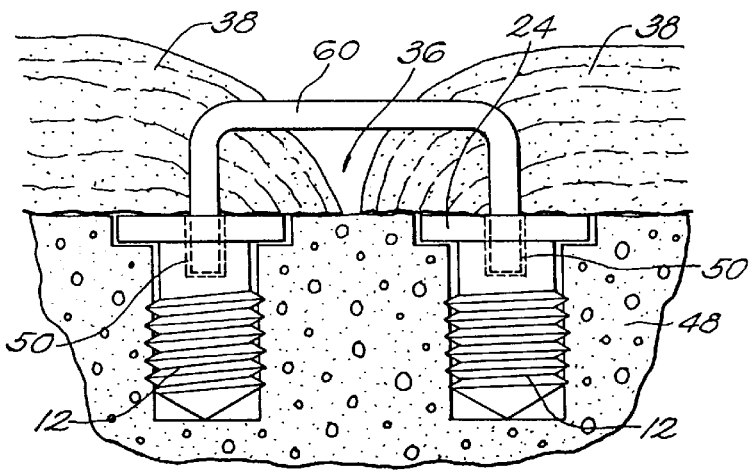
FIG. 10 is a side view of an alternate embodiment of the invention, in which multiple bone anchors are used to attach soft tissue to the bone with a band bonded into the bone anchors.
Figure 11:
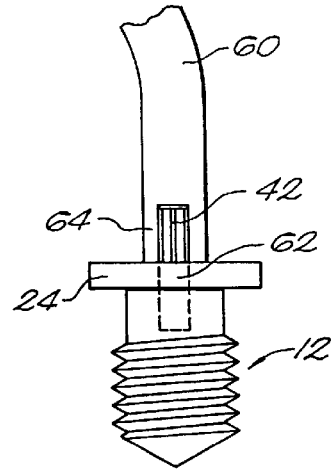
FIG. 11 is a side view of a bone anchor having an axially extending pin for engagement with a tubular portion of a band.
Figure 12:
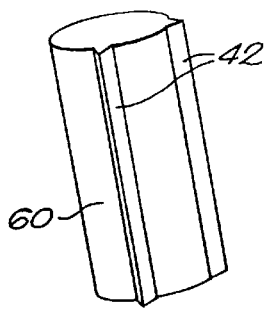
FIG. 12 is a perspective view of one form of a band, including energy directors.
Figure 13:
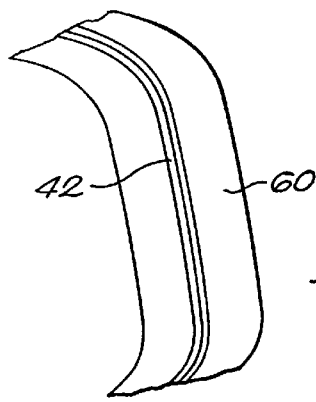
FIG. 13 is a perspective view of another form for a band.

Another embodiment of the invention is illustrated in FIG. 10. In this embodiment, more than one bone anchor element 12 is installed in a bone 48, and a bondable band 60 is fused to the bone anchors so as to define a tissue capture region 36 between the band and the bone, as shown in FIG. 9. The bone anchors 12 include a bore 50 into which an end of the band 60 can be inserted. Alternatively, as shown in FIG. 11, the bone anchor 12 can include a pin 62 extending axially above the hub 24, and the band 60 can include at its ends a tubular portion 64 which is designed to fit over the pin 62. The respective components (band and bone anchor) can include energy directors 42, as shown in FIGS. 11, 12 and 13, for focusing energy applied to either or both of them. Application of energy, such as, for example, ultrasonic energy, to the band 60, as previously described, will cause relative motion of the band and the anchor and localized melting of the components so as to fuse them together at the location of their mutual engagement. Thus, the band 60 can be set to a desired tension and/or to create a desired size for the tissue capture region 36 by selecting the length of the band and the depth to which the band is inserted into the anchor.

The band 60 can be of any dimension suitable for the application. As shown in FIGS. 12 and 13, the band can be round or flat. One or more bands may be used with the bone anchors 12, as needed.

Figure 14:
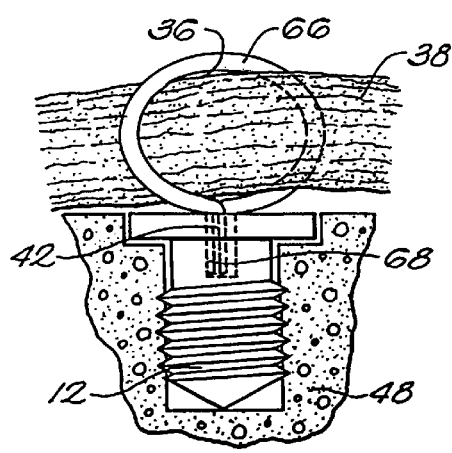
FIG. 14 is a side view of another embodiment of the assembly, in which a loop is fused with a bone anchor element to define a tissue capture region within the loop.

FIG. 14 illustrates still another embodiment of the assembly, in which the band is in the form of a loop 66 which is fused to the bone anchor element 12 to define a tissue capture region 36 within the confines of the loop. As described in connection with previous embodiments, the loop ends 68 and/or the bore 50 within the bone anchor element 12 can include energy directors 42. In addition, the loop ends 68 can include tubular portions to fit over corresponding pins extending axially from the bone anchor element, as described in connection with the embodiment of FIG. 11. The band forming the loop can be round or flat or other shape in cross-section, provided the band surface is designed to minimize trauma to the tissue 38 in contact with it. The size of the tissue capture region 36 within the loop can be varied, for example, by changing the length of the band forming the loop.

The band and anchor element are preferably made of a thermoplastic material which can be fused together upon application of ultrasonic or thermal energy.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

I claim:

1. A soft tissue fixation assembly for sutureless attachment of soft tissue to bone, the assembly comprising:

a bone anchor element extending along an axis and adapted for installation into a hole in a bone and including an anchor portion at a leading end and a drive portion at a drive end;

a joiner element extending along an axis; and one or more energy directing members extending axially on at least one of the anchor element and the joiner element for establishing a fusible interface therebetween, wherein the anchor element and the joiner element are adapted to be fused together in situ at said fusible interface upon application of energy to at least one of the joiner element and the anchor element, thereby defining a tissue capture region between them.

2. An assembly according to claim 1, wherein the joiner element is in the form of a post with a cap at one end, and wherein the anchor element includes protruding elements at a leading end thereof for substantially permanent installation of the anchor element into a bone, and a hub at a drive end of the anchor element.

3. An assembly according to claim 2, wherein the anchor element includes at least one bore for receiving at least a portion of the joiner element.

4. An assembly according to claim 3, wherein the one or more energy directing members includes one or more projections extending from at least one of the anchor element and the joiner element for focusing energy applied to at least one of the anchor element and the joiner element.

5. An assembly according to claim 4, wherein the projections extend from at least one of the bore of the anchor element and the post of the joiner element.

6. An assembly according to claim 2, wherein the joiner element includes one or more tissue contacting members adapted to project into and hold the soft tissue in place within the tissue capture region of the assembly.

7. An assembly according to claim 6, wherein the tissue contacting members include barbs extending toward the tissue capture region of the assembly.

8. An assembly according to claim 2, wherein the tissue capture region of the assembly is defined as an annular region around the joiner element between the cap of the post and the hub of the anchor element.

9. An assembly according to claim 8, wherein the hub of the anchor element is located at or near the drive end of the anchor element.

10. An assembly according to claim 8 wherein the hub of the anchor element is located between the leading and drive ends of the anchor element.

11. An assembly according to claim 1, wherein the energy is ultrasonic energy.

12. An assembly according to claim 1, wherein the energy is thermal energy.

13. A soft tissue fixation assembly for sutureless attachment of soft tissue to bone, the assembly comprising:

a bone anchor element adapted for installation into a hole in a bone and including an anchor portion at a leading end and a drive portion at a drive end; and a joiner element;

wherein the anchor element and the joiner element are adapted to be fused together in situ upon application of energy to at least one of the joiner element and the anchor element, thereby defining a tissue capture region between them, wherein the joiner element is in the form of a post with a cap at one end, and wherein the anchor element includes protruding elements at a leading end thereof for substantially permanent installation of the anchor element into a bone, and a hub at a drive end of the anchor element, wherein the joiner element includes a bore for receiving a corresponding pin portion of the anchor element.

14. An assembly according to claim 13, wherein at least one of the joiner element and the anchor element includes one or more energy directors for focusing energy applied to at least one of the anchor element and the joiner element.

15. An assembly according to claim 14, wherein the energy directors comprise a plurality of projections extending from at least one of the bore of the joiner element and the pin of the anchor element.

16. A method of fixing soft tissue to a bone without using sutures, the method comprising the steps of:

providing a soft tissue fixation assembly for sutureless attachment of soft tissue to bone, the assembly including a bone anchor element adapted for installation into a hole in a bone and including an anchor portion at a leading end and a drive portion at a trailing end thereof, and a joiner element, wherein the anchor element and the joiner element are adapted to be fused together in situ, thereby defining a tissue capture region between them;

drilling a hole into a bone at a desired location for installation of the anchor element therein;

installing the anchor element into the drilled hole:

placing a segment of soft tissue to be anchored to the bone over the anchor element in the bone;

mating the joiner element with the anchor element through the segment of soft tissue to capture the soft tissue segment within the tissue capture region between the joiner element and the anchor element; and fusing the joiner element to the anchor element, thereby fixing the soft tissue segment to the bone, wherein the step of fusing the joiner element to the anchor element comprises the step of transmitting energy to at least one of the joiner element and the anchor element to effect localized melting and fusing of interfering portions of the joiner element and the anchor element.

17. A method according to claim 16, wherein the energy is ultrasonic energy.

18. A method according to claim 16, wherein the energy is thermal energy.

19. A soft tissue fixation assembly for sutureless attachment of soft tissue to bone, the assembly comprising:

one or more bone anchor elements each extending along an axis and adapted for installation into respective holes in a bone, each bone anchor element including an anchor portion at a leading end and a drive portion at a drive end;

a band element extending along an axis; and one or more energy directing members extending axially on at least one of the bone anchor elements and said band element for establishing a fusible interface between said one or more bone anchor elements and said band element, wherein said band element is adapted for fused engagement with each anchor element at the fusible interface upon application of energy to at least one of the band element and the anchor elements, thereby defining a tissue capture region between the band element and the one or more bone anchor elements.

20. An assembly according to claim 19, comprising a pair of bone anchor elements, wherein the band element extends between opposed ends, wherein the ends of the band element are adapted for fused engagement with corresponding structures on the bone anchor elements.

21. An assembly according to claim 19, comprising a single bone anchor element, wherein the band element comprises a loop, wherein the ends of the loop are adapted for fused engagement with the bone anchor element, and wherein the tissue capture region is defined as the region within the loop.

22. An assembly according to claim 19, wherein the energy is ultrasonic energy.

23. An assembly according to claim 19, wherein the energy is thermal energy.

* * * * *